(12) United States Patent
Raulerson

(10) Patent No.: US 7,261,708 B2
(45) Date of Patent: Aug. 28, 2007

(54) REMOVABLE CATHETER HUB

(75) Inventor: J. Daniel Raulerson, Brewton, AL (US)

(73) Assignee: Medical Components, Inc., Harleysville, PA (US)

( * ) Notice: Subject to any disclaimer, the term of this patent is extended or adjusted under 35 U.S.C. 154(b) by 538 days.

(21) Appl. No.: 10/691,331

(22) Filed: Oct. 22, 2003

(65) Prior Publication Data
US 2004/0097903 A1 May 20, 2004

Related U.S. Application Data

(60) Provisional application No. 60/423,002, filed on Nov. 1, 2002, provisional application No. 60/422,726, filed on Oct. 31, 2002.

(51) Int. Cl.
*A61M 25/00* (2006.01)
(52) U.S. Cl. .................................... 604/523
(58) Field of Classification Search .............. 604/43, 604/93.01, 264, 523, 533, 537; 128/DIG. 6, 128/26
See application file for complete search history.

(56) References Cited

U.S. PATENT DOCUMENTS

| | | | |
|---|---|---|---|
| 3,957,082 A | 5/1976 | Fuson et al. |
| 4,037,599 A | 7/1977 | Raulerson |
| 4,895,561 A | 1/1990 | Mahurkar |
| 5,037,405 A | 8/1991 | Crosby |
| 5,059,170 A | 10/1991 | Cameron |
| 5,575,767 A | 11/1996 | Stevens |
| 5,947,953 A | 9/1999 | Ash et al. |
| 6,156,016 A | 12/2000 | Maginot |
| 6,190,349 B1 | 2/2001 | Ash et al. |
| 6,248,092 B1 | 6/2001 | Miraki et al. |
| 6,689,096 B1 | 2/2004 | Loubens |
| 6,695,832 B2 | 2/2004 | Schon et al. |
| 6,719,727 B2 | 4/2004 | Brimhall et al. |
| 2002/0099326 A1 | 7/2002 | Wilson et al. |
| 2002/0099327 A1 | 7/2002 | Wilson et al. |
| 2002/0107475 A1 | 8/2002 | Maginot |
| 2002/0120224 A1 | 8/2002 | Zia et al. |

*Primary Examiner*—LoAn H. Thanh
(74) *Attorney, Agent, or Firm*—Anton P. Ness

(57) ABSTRACT

A removable hub (100) for a catheter (170) including a lower portion (110) having a lower proximal end (114), a lower distal end (112), and a lower channel (116, 118, 120) extending between the lower proximal end and the lower distal end. The catheter hub (100) further includes an upper portion (130) having an upper proximal end (134), an upper distal end (132), and an upper channel (136,138,140) extending between the upper proximal end and the upper distal end. The catheter hub (100) further includes a hinge (150) connecting the lower portion and the upper portion and a lock (152a, 152b, 156a, 156b) for releasably securing the lower portion and the upper portion to each other, distal from the hinge. When the lower portion is releasably secured to the upper portion, the lower channel and the upper channel form a passageway (182, 184, 186).

36 Claims, 7 Drawing Sheets

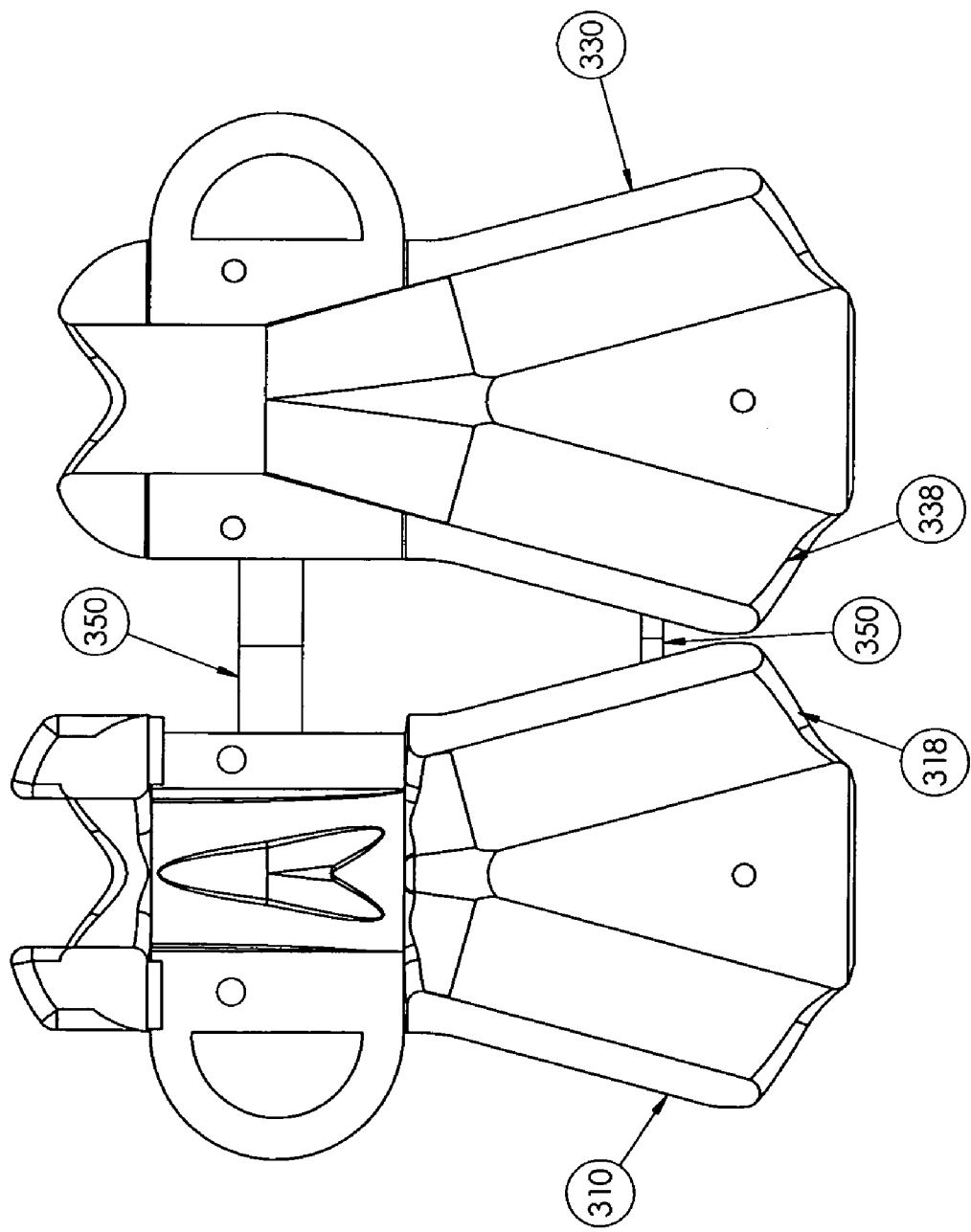

REMOVABLE CATHETER HUB

CROSS REFERENCE TO RELATED APPLICATIONS

The present application claims priority from U.S. Provisional Patent Application Ser. No. 60/422,726, filed Oct. 31, 2002, and from U.S. Provisional Patent Application Ser. No. 60/423,002, filed Nov. 1, 2000.

FIELD OF THE INVENTION

The present invention relates to a catheter hub that can be slidably disposed along a portion of a length of a catheter assembly and/or removed from the catheter assembly.

BACKGROUND OF THE INVENTION

Catheters for the introduction or removal of fluids may be located in various venous locations and cavities throughout the body for introduction or removal of these fluids. Such catheterization may be performed by using a single catheter having multiple lumens. A typical example of a multiple lumen catheter is a dual lumen catheter in which one lumen introduces fluid and the other lumen removes fluid.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the guide wire within the vessel. The guide wire projects beyond the surface of the skin. At this point, several options are available to a surgeon for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire, for example, for insertion of small diameter dual lumen catheters. If the catheter to be inserted is significantly larger than the guide wire, a dilator device is passed over the guide wire to enlarge the hole. The dilator is removed and the catheter is then passed over the guide wire. After the catheter is inserted, the guide wire is removed.

For chronic catheterization, in which the catheter is intended to remain inside the patient for an extended period of time, such as for weeks or even months, it is typically desired to subcutaneously tunnel the catheter using various tunneling techniques. The catheter is typically tunneled into the patient prior to inserting the catheter into the patient's vein. The catheter typically includes a catheter ingrowth cuff that allows skin tissue forming the subcutaneous tunnel, to grow into the ingrowth cuff to secure the catheter subcutaneously to the patient. The catheter also typically includes a hub that extends proximally of the subcutaneous tunnel. The hub usually includes at least one suture wing that allows the surgeon to suture the hub to the patient's skin, to further secure the catheter to the patient.

There may be times when it is more advantageous, such as depending on the patient or the implanting surgeon's skill, to perform the tunneling after the catheter is implanted in the patient. For some catheters, though, such as multiple lumen catheters with a hub and with bonded luers on the proximal ends of the catheters, it is impractical to perform the tunneling after the catheter is installed in the patient. It would be beneficial to provide a catheter assembly having a hub configuration that provides a surgeon with alternative installation procedures for installing the catheter that better suit either the patient's needs or the surgeon's skills. Further, while catheters are provided to surgeons in standard sizes, patients come in all different sizes and in all different conditions, and what may be a suitable place to suture a hub in one patient may be a poor place to suture a hub in another patient. It would therefore be beneficial to provide a hub that can be disposed along the catheter to a particular location as determined by the surgeon, based on the size and condition of each particular patient.

Further, since the catheter is intended to be in the patient for an extended period of time, the hub, which may be fairly large as compared to the diameter of the catheter, may cause inconvenience to the patient. It would therefore be beneficial to be able to remove the hub at some time after installation of the catheter so that the hub does not inconvenience the patient.

BRIEF SUMMARY OF THE INVENTION

Briefly, the present invention provides a catheter hub. The catheter hub comprises a lower portion having a lower distal end and a lower proximal end. The lower distal end includes a lower distal channel extending from the lower distal end toward the lower proximal end. The lower proximal end includes first and second lower proximal channels extending from the lower proximal end toward the lower distal end such that the first and second lower proximal channels fluidly communicate with the lower distal channel. The hub also comprises an upper portion having an upper distal end and an upper proximal end. The upper distal end includes an upper distal channel extending from the lower distal end toward the lower proximal end. The upper proximal end includes first and second upper proximal channels extending from the upper proximal end toward the upper distal end such that the first and second upper proximal channels fluidly communicate with the upper distal channel. The hub further comprises a hinge connecting the lower portion and the upper portion and a locking section for releasably securing the lower portion and the upper portion to each other, distal from the hinge. When the lower portion is releasably secured to the upper portion, the lower distal channel and the upper distal channel form a distal passageway, the first lower proximal channel and the first upper proximal channel form a first proximal passageway and the second lower proximal channel and the second upper proximal channel form a second proximal passageway.

Additionally, the present invention provides a catheter hub. The catheter hub comprises a lower portion having a lower proximal end, a lower distal end, and a lower channel extending between the lower proximal end and the lower distal end. The catheter hub further comprises an upper portion having an upper proximal end, an upper distal end, and an upper channel extending between the upper proximal end and the upper distal end. The catheter hub further comprises a hinge connecting the lower portion and the upper portion and a locking section for releasably securing the lower portion and the upper portion to each other, distal from the hinge. When the lower portion is releasably secured to the upper portion, the lower channel and the upper channel form a passageway.

Further, the present invention provides a catheter hub. The catheter hub comprises a lower portion having a lower distal end and a lower proximal end. The lower distal end includes a lower distal channel extending from the lower distal end toward the lower proximal end. The lower proximal end includes first and second lower proximal channels extending from the lower proximal end toward the lower distal end. The first and second lower proximal channels fluidly communicate with the lower distal channel. The hub further includes an upper portion having an upper distal end and an upper proximal end, a hinge connecting the lower portion and the upper portion, and a locking section for releasably securing the lower portion and the upper portion to each other, distal from the hinge. When the lower portion is releasably secured to the upper portion, the lower distal channel and the upper portion form a distal passageway, the first lower proximal channel and the upper portion form a first proximal passageway and the second lower proximal channel and the upper portion form a second proximal passageway.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 7 is a top plan view of a catheter hub, in an open position, according to a third embodiment of the present invention.

DETAILED DESCRIPTION OF THE INVENTION

Figure 1:
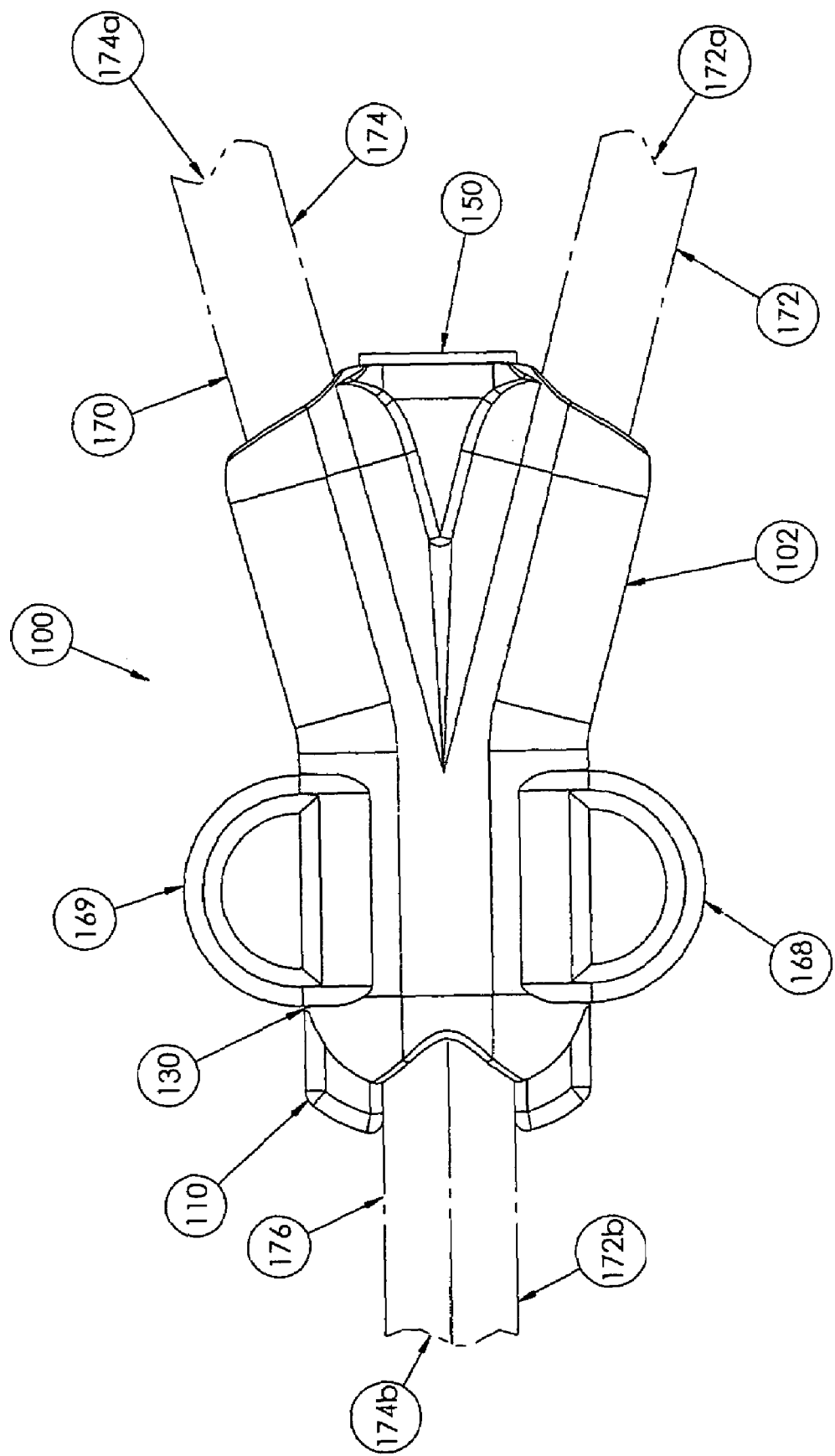
FIG. 1 is a plan view showing a catheter hub according to a first embodiment of the present invention as the hub is connected to a multilumen catheter.

In the drawings, like numerals indicate like elements throughout. Certain terminology is used herein for convenience only and is not to be taken as a limitation on the present invention. The words "proximal" and "distal" refer to directions toward the right side and left side, respectively, of a catheter hub 100 shown in FIG. 1. The terminology includes the words above specifically mentioned, derivatives thereof, and words of similar import. The following describes a preferred embodiment of the invention. However, it should be understood, based on this disclosure, that the invention is not limited by the preferred embodiment described herein.

Referring now to FIG. 1, the catheter hub 100 is shown. The hub 100 may be used in multi-lumen catheters 170, such as the SPLIT STREAM™ catheter, manufactured by Medical Components, Inc. of Harleysville, Pa., which is disclosed in U.S. Provisional Patent Application Ser. No. 60/422,726, filed on Oct. 31, 2002, and U.S. Provisional Patent Application Ser. No. 60/423,002, filed on Nov. 1, 2002, which are both incorporated by reference herein in their entireties.

Such a catheter 170 is shown in dashed lines in FIG. 1. The catheter 170 includes a first, or arterial lumen 172 and a second, or venous lumen 174. The arterial lumen 172 serves to draw blood from a patient's body during hemodialysis, while the venous lumen 174 serves to return the blood to the patient's body after the blood has been dialyzed. The lumens 172, 174 are separated to allow fittings, such as connectors, clamps, and/or luer locks to be connected to proximal ends 172a, 174a of each of the lumens 172, 174, such as those shown in U.S. patent application Ser. No. 60/423,002.

Preferably, the catheter 170 is inserted into the patient without the hub 100 being connected to the catheter 170. After the catheter 170 is inserted into the patient, the hub 100 is connected to the catheter 170 such that the lumens 172, 174 converge within the hub 100 to form a unitary catheter body 176 comprised of distal ends 172b, 174b of the first and second lumens 172, 174, respectively. A portion of the distal ends 172b, 174b of the lumens 172, 174 that will be immediately distal of the hub 100 are inserted subcutaneously through the patient's skin tissue, while remaining, most distal portions of the distal ends 172a, 172b are inserted into the blood vessel being catheterized. After the implanting surgeon is satisfied with the placement of the most distal portions of the distal ends 172a, 172b of the catheter 170 in the patient's blood vessel, the hub 100 is connected to the catheter 170.

Figure 2:
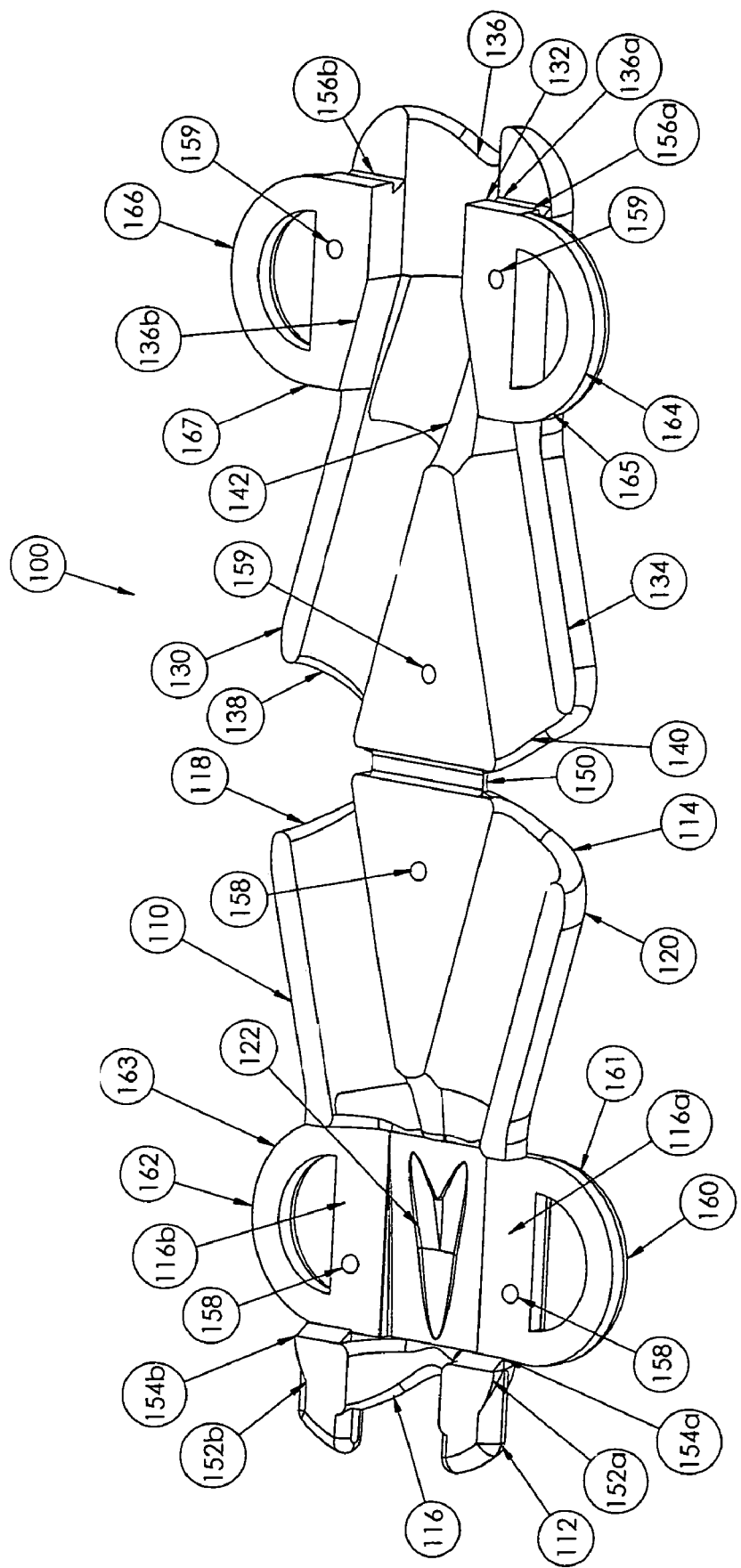
FIG. 2 is perspective view of the hub of FIG. 1, in an open position.
Figure 3:
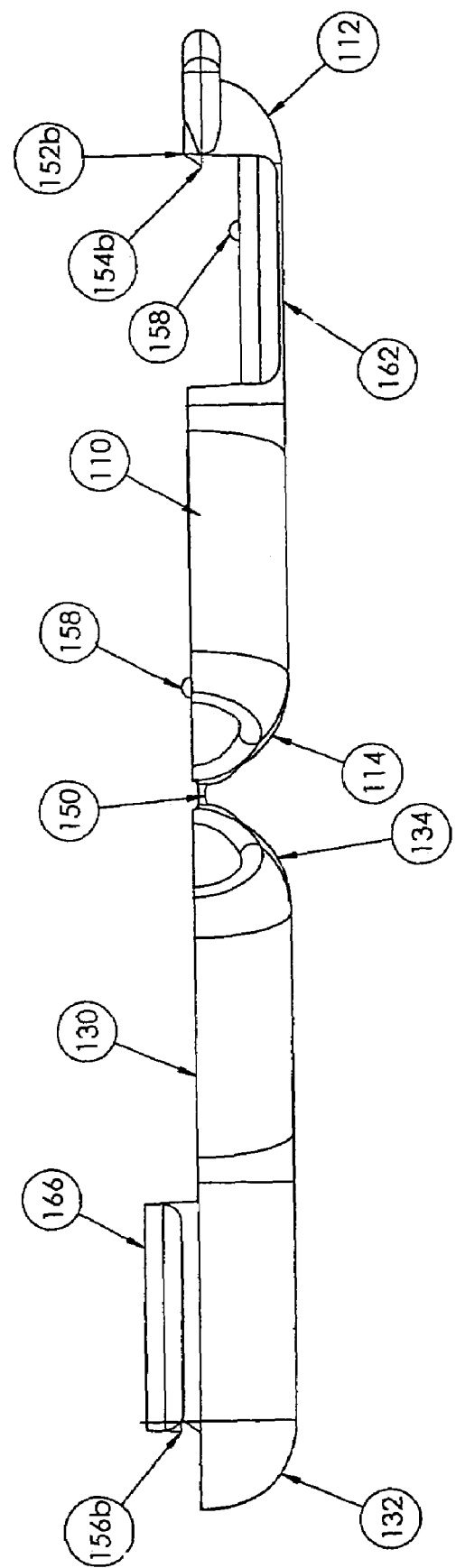
FIG. 3 is a side elevational view of the hub of FIG. 2.

The hub 100 comprises a unitary body 102, best seen in FIGS. 2 and 3, that is preferably constructed from a polymer, such as polypropylene, although those skilled in the art will recognize that other suitable materials may be used. The body 102 includes a bottom portion 110 and a top portion 130 that generally fits over the lower portion 110 when the hub 100 is in a closed position, as shown in FIG. 1. A hinge 150 connects the lower portion 110 and the upper portion 130 at the hinge 150.

FIGS. 2 and 3 show the hub 100 in an open position, with the catheter 170 having been removed from the hub 100, with the lower portion 110 on the left side of each Figure and the upper portion 130 on the right side of each Figure. The lower portion 110 includes a lower distal end 112 and a lower proximal end 114. The lower distal end 112 includes a lower distal channel 116 that extends from the lower distal end 112 toward the lower proximal end 114. The lower proximal end 114 includes first and second lower proximal channels 118, 120 that extend from the lower proximal end 114 toward the lower distal end 112. The first and second lower proximal channels 118, 120 fluidly communicate with the lower distal channel 116 at a junction 122. The lower distal channel 116 has openings 116a, 116b on either side between the junction 122 and the lower distal end 112.

The upper portion 130 includes an upper distal end 132 and an upper proximal end 134. The upper distal end 132 includes an upper distal channel 136 that extends from the upper distal end 132 toward the upper proximal end 134. The upper proximal end 134 includes first and second upper proximal channels 138, 140 that extend from the upper proximal end 134 toward the upper distal end 132. The first and second upper proximal channels 138, 140 fluidly communicate with the upper distal channel 136 at a junction 142. The upper distal channel 136 includes recessed portions 136a, 136b on either side between the junction 142 and the upper distal end 132, such that, when the hub 100 is in a closed position, each recessed portion 136a, 136b opposes a respective opening 116a, 116b in the lower distal channel 116.

The hinge 150 connects the lower portion 110 and the upper portion 130 at the lower proximal end 114 of the lower portion 110 and the upper proximal end 134 of the upper portion 130. The hinge 150 is disposed between the first and second lower proximal channels 118, 120, respectively. Preferably, the hinge 150 is a living hinge, constructed from the same material as the body 102. A locking section for releasably securing the lower proximal end 112 of the lower portion 110 and the upper proximal end 134 of the upper portion 130 to each other is disposed on each of the lower and upper portions 110, 130, distal of the hinge 150 and includes first and second tabs 152a, 152b 112 of the lower portion 110 on either side of the lower distal channel 116. Each tab 152a, 152b includes a respective lower beveled lip 154a, 154b that extends generally toward the hinge 150. Each lower beveled lip 154a, 154b is releasably engageable with an upper beveled lip 156a, 156b, respectively, when the lower portion 110 is pivoted about the hinge 150 to engage the upper portion 130.

A plurality of locator pins 158 are disposed along the lower portion 110, with corresponding locator recesses 159 being located along the upper portion 130 such that each locator pin 158 is disposed within a corresponding locator recess 159 when the lower portion 110 and the upper portion 130 are pivoted into engagement with each other. The locator pins 158 and the locator recesses 159 prevent the lower portion 110 and the upper portion 130 from sliding transversely with respect to each other when the lower portion 110 and the upper portion 130 are engaged.

Hub 100 is provided with a securing section for being securable to a patient. A plurality of lower suture wings 160, 162 extend outwardly from the lower portion 110, preferably proximate to the first and second lower beveled lips 154a, 154b, respectively, and include a generally flat face 161, 163, respectively. A plurality of upper suture wings 164, 166 extend outwardly from the upper portion 130, preferably proximate to the first and second upper beveled lips 156a, 156b, respectively, and include a generally flat face 165, 167, respectively. When the hub 100 is in the closed position, the flat face 161 engages the flat face 165 and the flat face 163 engages the flat face 167 to form a single suture wing assembly 168, 169, respectively, on either side of the hub body 102. While suture wing assemblies 168, 169 are preferred, those skilled in the art will recognize that at least one of the suture wing assemblies 168, 169 may be omitted without departing from the scope of the present invention. The suture wing assemblies 168, 169 are used to releasably secure the hub 100 to the exterior of the patient's body, as is well known in the art.

In use, a catheter 170 is inserted without the hub 100 attached, and the proximal end of the catheter 170 is subcutaneously tunneled according to known techniques. The proximal end of the catheter 170 may be subcutaneously tunneled prior to or after insertion of the distal end of the catheter 170 into the patient.

The hub 100 is then connected to the catheter by opening the hub 100 to the position shown in FIG. 2. The first lumen 172 is disposed in the first lower proximate channel 118 and the second lumen 174 is disposed within the second lower proximate channel 120. The unitary catheter body 176 is disposed in the lower distal channel 122. The upper portion 130 is pivoted about the hinge 150 so that the first upper proximate channel 138 is disposed over the first lumen 172 and the second upper proximate channel 140 is disposed over the second lumen 174. The upper distal channel 142 is disposed over the unitary catheter body 176. Each lower beveled lip 154a, 154b interlockingly fits with a respective upper beveled lip 156a, 156b such that the lower portion 110 and the upper portion 130 are releasably secured to each other remote from hinge 150. The locator pins 158 are each disposed within a respective locator recess 159. The hub 100 is now releasably connected to the catheter 170.

Figure 4:
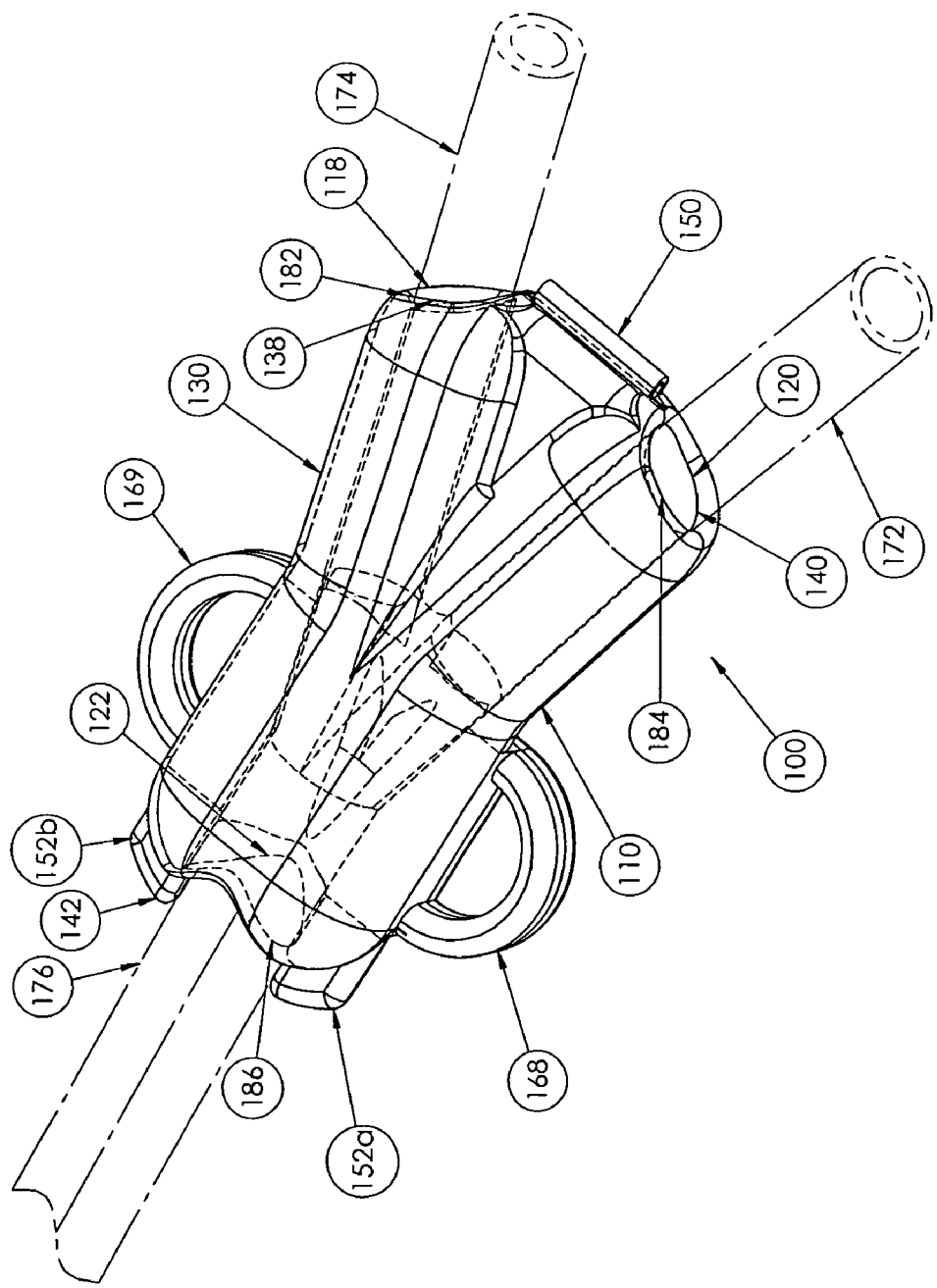
FIG. 4 is a perspective view of the hub of FIGS. 1–3 in a closed position.

As seen in FIG. 4, when the hub 100 is in the closed position, the first lower proximal channel 118 and the first upper proximal channel 138 form a first proximal passageway 182, the second lower proximal passageway 120 and the second upper proximal passageway 140 form a second proximal passageway 184. The lower distal channel 122 and the upper distal channel 142 form a distal passageway 186. The distal passageway 186 fluidly communicates with each of the first and second proximal passageways 182, 184 so that the first catheter lumen 172 is disposable within the first proximal passageway 182 and the second catheter lumen 174 is disposable within the second proximal passageway 184, with the unitary catheter body 176 being disposable within the distal passageway 186.

The hub 100 is then preferably sutured to the patient's skin by applying sutures through the suture wing assemblies 168, 169, as is well known in the art. The hub 100 is used to secure the catheter 170 to the patient until the ingrowth cuff is secured in the subcutaneous tunnel. When the surgeon determines that the catheter 170 is securely attached to the patient, the surgeon may opt to remove the hub 100 by cutting the sutures from the suture wing assemblies 168, 169. The first and second tabs 152a, 152b are depressed away from the upper portion 130 so each lower beveled lip 154a, 154b disengages from each respective upper beveled lip 156a, 156b. The upper portion 130 is pivoted about the hinge 150 so that the catheter 170 is released from the hub 100. The hub 100 may then be removed from the catheter 170.

Figure 5:
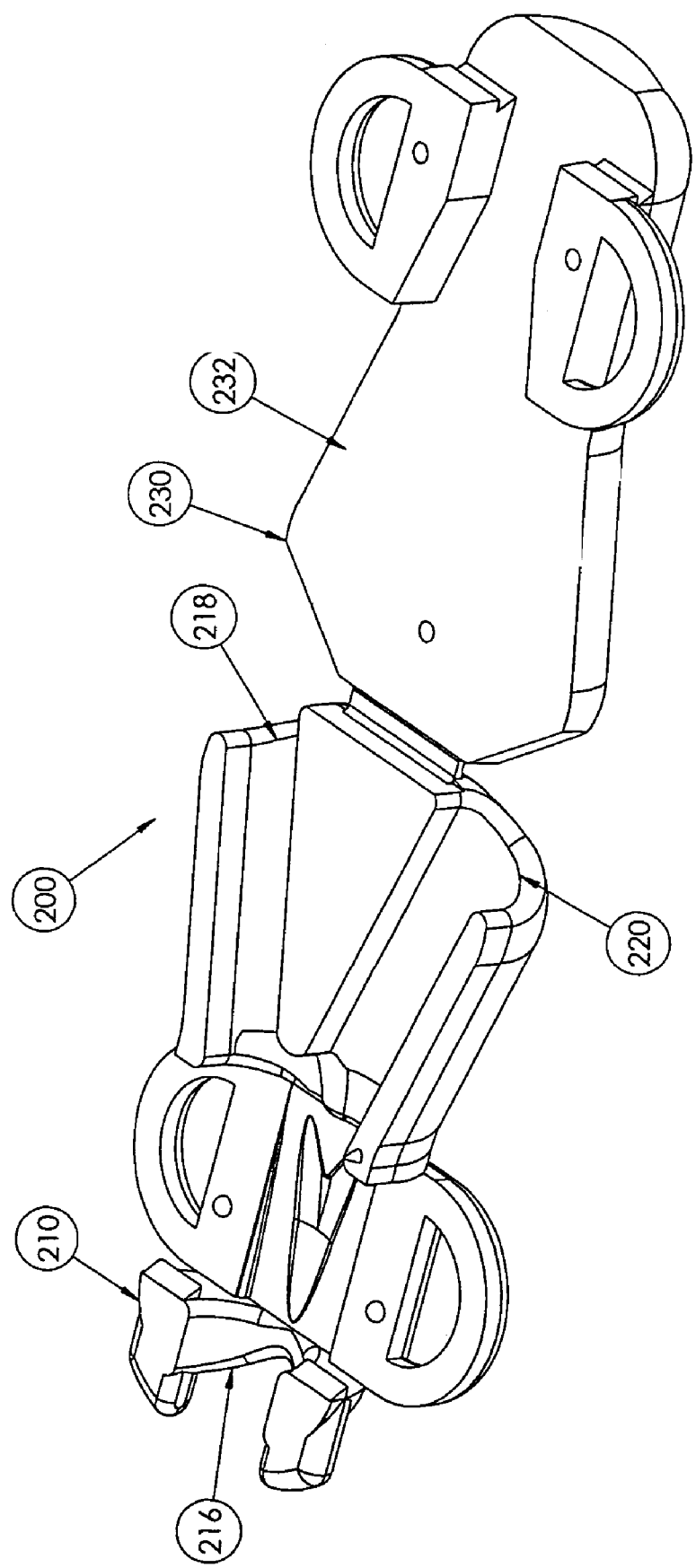
FIG. 5 is a perspective view of a catheter hub, in an open position, according to a second embodiment of the present invention.
Figure 6:
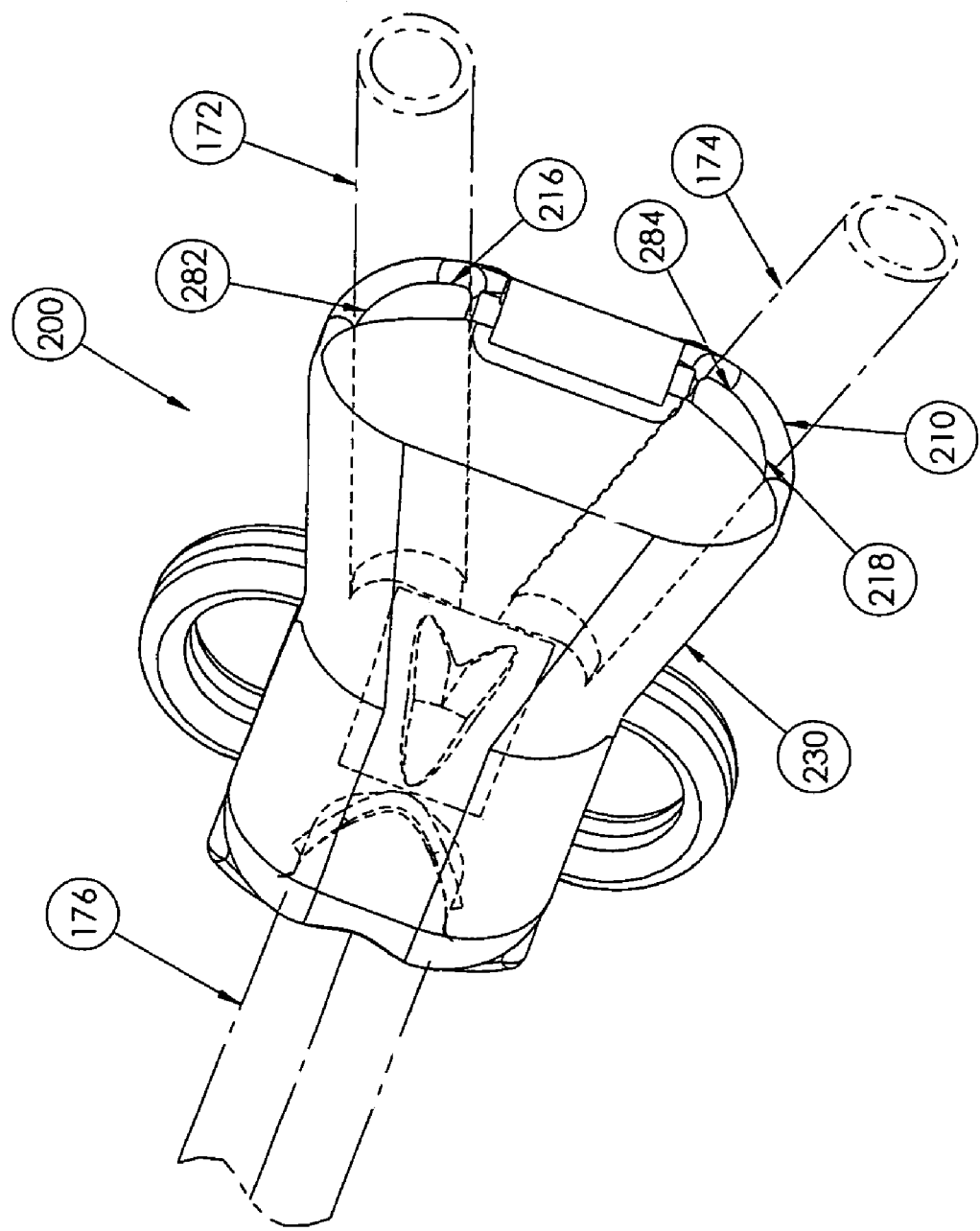
FIG. 6 is a perspective view of the hub of FIG. 5 in a closed position.

An alternate embodiment of a hub 200 is shown in FIGS. 5 and 6. The hub 200 includes a lower portion 210 and an upper portion 230. The hub 200 is similar to the hub 100 with the exception that channels 216, 218, 220 in the lower portion 210 are deeper than corresponding channels 116, 118, 120 previously shown in FIG. 2. The channels 216, 218, 220 are sufficiently deep to fully encompass catheter lumens 172, 174 such that channels are not required in the upper portion 230. Consequently, the upper portion 230 preferably includes a generally flat interior surface 232. The hub 200 operates in a similar manner as the hub 100 above. When the hub 100 is in a closed position, as shown in FIG. 6, the first lower proximal channel 218 and the interior surface 232 form a first proximal passageway 282, the second lower proximal channel 220 and the interior surface 232 form a second proximal passageway 284, and the lower distal channel 216 and the interior surface 232 form a distal passageway 286.

Another alternate embodiment of a hub 300 is shown in FIG. 7. The hub 300 includes a lower portion 310 and an upper portion 330. The hub 300 is similar to the hub 100 previously shown in FIG. 2, with the exception that the hinge 150 connecting the lower distal end 114 and the upper distal end 134 of the hub 100 have been removed and replaced with a hinge 350 hingedly connecting the first lower proximal channel 318 and the first upper proximal channel 338. Further, suture wings 162, 166 have been removed to allow the lower portion 310 to pivot about the hinge 350 to releasably engage the upper portion 330.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A catheter hub comprising:
a lower portion having a lower distal end and a lower proximal end, wherein the lower distal end includes a lower distal channel extending from the lower distal end toward the lower proximal end and wherein the lower proximal end includes first and second lower proximal channels extending from the lower proximal end toward the lower distal end, wherein the first and second lower proximal channels fluidly communicate with the lower distal channel;
an upper portion having an upper distal end and an upper proximal end, wherein the upper distal end includes an upper distal channel extending from the lower distal end toward the lower proximal end and wherein the upper proximal end includes first and second upper proximal channels extending from the upper proximal end toward the upper distal end, wherein the first and second upper proximal channels fluidly communicate with the upper distal channel;
a hinge connecting the lower portion and the upper portion; and
a locking section for releasably securing the lower portion and the upper portion to each other, remote from the hinge,
wherein, when the lower portion is releasably secured to the upper portion, the lower distal channel and the upper distal channel form a distal passageway, the first lower proximal channel and the first upper proximal channel form a first proximal passageway and the second lower proximal channel and the second upper proximal channel form a second proximal passageway.

2. The catheter hub according to claim 1, wherein the hinge is disposed at a proximal end of the hub and between the first and second lower proximal channels, and the locking section is disposed at the distal end of the hub.

3. The catheter hub according to claim 1, wherein at least one of the lower and upper portions comprises a securing section for releasably securing the hub to a body.

4. The catheter hub according to claim 1, wherein the lower portion and the upper portion are releasably secured to each other by an interlocking engagement between the lower portion and the upper portion.

5. The catheter hub according to claim 1, wherein the lower portion comprises at least one of a locating pin and a like number of recesses, wherein the upper portion comprises the other of the at least one locating pin and the like number of recesses, and wherein, when the lower portion is releasably secured to the upper portion, each of the at least one pin is disposed within a respective one of each of the like number of recesses.

6. The catheter hub according to claim 1, wherein the hinge is a living hinge.

7. The catheter hub according to claim 1, wherein the catheter hub is constructed from polypropylene.

8. The catheter hub according to claim 1, wherein the distal passageway fluidly communicates with each of the first and second proximal passageways.

9. The catheter hub according to claim 1, further comprising at least one suture wing extending from at least one of the lower portion and the upper portion.

10. The catheter hub according to claim 1, wherein a first catheter lumen is disposable in the first proximal passageway and the distal passageway, and wherein a second catheter lumen is disposable in the second proximal passageway and the distal passageway.

11. A catheter hub comprising:
a lower portion having a lower proximal end, a lower distal end, and a lower channel extending between the lower proximal end and the lower distal end and having openings at distal and proximal ends thereof;
an upper portion having an upper proximal end, an upper distal end, and an upper channel extending between the upper proximal end and the upper distal end and having openings at distal and proximal ends thereof;
a hinge connecting the lower portion and the upper portion; and
a locking section for releasably securing the lower portion and the upper portion to each other, remote from the hinge,
wherein, when the lower portion is releasably secured to the upper portion, the lower channel and the upper channel form a passageway and having openings at distal and proximal ends thereof.

12. The catheter hub according to claim 11, wherein, proximate to the lower proximal end, the lower channel comprises a plurality of lower channels.

13. The catheter hub according to claim 12, wherein, proximate to the upper proximal end, the upper channel comprises a like plurality of upper channels.

14. The catheter hub according to claim 13, wherein, when the lower portion is releasably secured to the upper portion, the plurality of lower channels and the like plurality of upper channels form a like plurality of passageways.

15. The catheter hub according to claim 14, wherein a like plurality of catheter lumens are each disposable within one of the like plurality of passageways.

16. The catheter hub according to claim 11, wherein at least one of the lower and upper portions comprises a securing section for releasably securing the hub to a body.

17. The catheter hub according to claim 11, wherein the lower portion and the upper portion are releasably secured to each other by an interlocking engagement between the lower portion and the upper portion.

18. The catheter hub according to claim 11, wherein the lower portion comprises at least one of a locating pin and a like number of recesses, wherein the upper portion comprises the other of the at least one locating pin and the like number of recesses, and wherein, when the lower portion is releasably secured to the upper portion, each of the at least one pin is disposed within a respective one of each of the like number of recesses.

19. The catheter hub according to claim 11, wherein the hinge is a living hinge.

20. The catheter hub according to claim 11, wherein the catheter hub is constructed from polypropylene.

21. The catheter hub according to claim 11, further comprising at least one suture wing extending from at least one of the lower portion and the upper portion.

22. A catheter hub comprising:
a lower portion having a lower distal end and a lower proximal end, wherein the lower distal end includes a lower distal channel extending from the lower distal end toward the lower proximal end and wherein the lower proximal end includes first and second lower proximal channels extending from the lower proximal end toward the lower distal end, wherein the first and second lower proximal channels fluidly communicate with the lower distal channel;
an upper portion having an upper distal end and an upper proximal end;

a hinge connecting the lower portion and the upper portion; and a locking section for releasably securing the lower portion and the upper portion to each other, remote from the hinge, wherein, when the lower portion is releasably secured to the upper portion, the lower distal channel and the upper portion form a distal passageway, the first lower proximal channel and the upper portion form a first proximal passageway and the second lower proximal channel and the upper portion form a second proximal passageway.

23. The catheter hub according to claim 22, wherein the hinge is disposed between the first and second lower proximal channels.

24. The catheter hub according to claim 22, wherein at least one of the lower and upper portions comprises a securing section for releasably securing the hub to a body.

25. The catheter hub according to claim 22, wherein the lower portion and the upper portion are releasably secured to each other by an interlocking engagement between the lower portion and the upper portion.

26. The catheter hub according to claim 22, wherein the lower portion comprises at least one of a locating pin and a like number of recesses, wherein the upper portion comprises the other of the at least one locating pin and the like number of recesses, and wherein, when the lower portion is releasably secured to the upper portion, each of the at least one pin is disposed within a respective one of each of the like number of recesses.

27. The catheter hub according to claim 22, wherein the hinge is a living hinge.

28. The catheter hub according to claim 22, wherein the catheter hub is constructed from polypropylene.

29. The catheter hub according to claim 22, wherein the distal passageway fluidly communicates with each of the first and second proximal passageways.

30. The catheter hub according to claim 22, further comprising at least one suture wing extending from at least one of the lower portion and the upper portion.

31. The catheter hub according to claim 22, wherein a first catheter lumen is disposable in the first proximal passageway and the distal passageway, and wherein a second catheter lumen is disposable in the second proximal passageway and the distal passageway.

32. The catheter hub according to claim 1, wherein the hinge connecting the lower portion and the upper portion is disposed along one side of the catheter hub.

33. The catheter hub according to claim 32, wherein the hinge comprises two hinge portions spaced longitudinally apart along the one side.

34. The catheter hub according to claim 11, wherein the hinge connecting the lower portion and the upper portion is disposed along one side of the catheter hub.

35. The catheter hub according to claim 34, wherein the hinge comprises two hinge portions spaced longitudinally apart along the one side.

36. A catheter hub comprising:

a lower portion having a lower proximal end and a lower distal end, an upper portion having an upper proximal end and an upper distal end, at least one of the lower and upper portion having a distal channel extending from a distal opening at a respective distal end to and in fluid communication with proximal channels having respective proximal openings at a respective proximal end thereof, a hinge connecting the lower portion and the upper portion; and a locking section for releasably securing the lower portion and the upper portion to each other, remote from the hinge, wherein, when the lower portion is releasably secured to the upper portion, the lower portion and the upper portion form a distal passageway from the distal hub end to proximal passageways at a proximal hub end.

* * * * *